(12) United States Patent
Matsubara et al.

(10) Patent No.: US 9,693,912 B2
(45) Date of Patent: Jul. 4, 2017

(54) SPUNBONDED NONWOVEN FABRICS

(75) Inventors: Akio Matsubara, Ichihara (JP); Kenichi Suzuki, Ichihara (JP); Shingo Kajiyama, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 13/984,383

(22) PCT Filed: Feb. 15, 2012

(86) PCT No.: PCT/JP2012/053575
§ 371 (c)(1),
(2), (4) Date: Aug. 8, 2013

(87) PCT Pub. No.: WO2012/111723
PCT Pub. Date: Aug. 23, 2012

(65) Prior Publication Data
US 2013/0317469 A1    Nov. 28, 2013

(30) Foreign Application Priority Data
Feb. 15, 2011    (JP) .................................. 2011-029917

(51) Int. Cl.
*A61F 13/15*    (2006.01)
*A61F 13/538*    (2006.01)
(Continued)

(52) U.S. Cl.
CPC ............ *A61F 13/538* (2013.01); *B32B 5/022* (2013.01); *B32B 5/26* (2013.01); *D01D 5/24* (2013.01);
(Continued)

(58) Field of Classification Search
CPC ............ A61F 13/538; A61F 2013/5383; A61F 2013/5386
(Continued)

(56) References Cited

U.S. PATENT DOCUMENTS 4,627,811 A    12/1986    Greiser et al.
5,256,358 A    10/1993    Shiraki et al.
(Continued)

FOREIGN PATENT DOCUMENTS

EP    2216435 A1    8/2010
JP    60-155765 A    8/1985
(Continued)

OTHER PUBLICATIONS

Office Action issued on Oct. 16, 2014, by the Korean Patent Office in corresponding Korean Patent Application No. 10-2013-7022313 (6 pages).
(Continued)

*Primary Examiner* — Jacqueline Stephens
(74) *Attorney, Agent, or Firm* — Buchanan, Ingersoll & Rooney PC

(57) ABSTRACT

An object of the invention is to obtain spunbonded nonwoven fabrics including thin hollow fibers which have excellent lightweight properties and uniformity as well as exhibit high strength and flexibility. An aspect of the invention is directed to a spunbonded nonwoven fabric including hollow fibers of a propylene polymer, the hollow fibers satisfying the following requirements (a) to (c): (a) the C-axis orientation is at least 0.85, (b) the average fiber diameter is 5 to 20 μm, and (c) the hollowness is 5 to 30%.

13 Claims, 4 Drawing Sheets

(51) Int. Cl.
*D04H 3/007* (2012.01)
*D04H 3/018* (2012.01)
*D04H 3/10* (2012.01)
*D04H 3/14* (2012.01)
*D01D 5/24* (2006.01)
*D01F 6/06* (2006.01)
*B32B 5/02* (2006.01)
*B32B 5/26* (2006.01)
*D04H 3/16* (2006.01)
*D04H 1/4391* (2012.01)
*A61F 13/49* (2006.01)

(52) U.S. Cl.
CPC .............. *D01F 6/06* (2013.01); *D04H 1/4391* (2013.01); *D04H 3/007* (2013.01); *D04H 3/018* (2013.01); *D04H 3/10* (2013.01); *D04H 3/14* (2013.01); *D04H 3/16* (2013.01); *A61F 13/49017* (2013.01); *A61F 13/49019* (2013.01); *A61F 2013/5383* (2013.01); *A61F 2013/5386* (2013.01); *B32B 2250/20* (2013.01); *B32B 2262/0253* (2013.01); *B32B 2555/00* (2013.01); *B32B 2555/02* (2013.01); *Y10T 442/612* (2015.04)

(58) Field of Classification Search
USPC ....... 604/367, 365, 366, 370, 372, 374, 375, 604/376
See application file for complete search history.

(56) References Cited

U.S. PATENT DOCUMENTS

| | | | | |
|---|---|---|---|---|
| 5,277,976 | A | * | 1/1994 | Hogle .................... D01D 5/253 428/395 |
| 5,466,410 | A | * | 11/1995 | Hills ........................ 264/172.11 |
| 6,368,990 | B1 | | 4/2002 | Jennergren et al. |
| 6,838,154 | B1 | * | 1/2005 | Varona et al. ................ 428/152 |
| 8,147,956 | B2 | | 4/2012 | Miyauchi et al. |
| 2004/0170836 | A1 | | 9/2004 | Bond et al. |
| 2010/0255255 | A1 | | 10/2010 | Kawakami et al. |
| 2010/0273947 | A1 | | 10/2010 | Miyauchi et al. |
| 2010/0292662 | A1 | | 11/2010 | Matsubara et al. |
| 2011/0136402 | A1 | | 6/2011 | Matsubara et al. |

FOREIGN PATENT DOCUMENTS

| | | |
|---|---|---|
| JP | 61-174416 A | 8/1986 |
| JP | 03-287848 A | 12/1991 |
| JP | 04-108108 A | 4/1992 |
| JP | 04-163353 A | 6/1992 |
| JP | 3442896 B2 | 9/2003 |
| JP | 2007-046224 A | 2/2007 |
| JP | 3883818 B2 | 2/2007 |
| JP | 2010-179222 A | 8/2010 |
| KR | 10-2010-0074274 A | 7/2010 |
| WO | 00/44411 A1 | 8/2000 |
| WO | 2004/063434 A1 | 7/2004 |
| WO | WO 2009/063892 A1 | 5/2009 |
| WO | WO 2010/024268 A1 | 3/2010 |
| WO | WO 2012/077638 A1 | 6/2012 |

OTHER PUBLICATIONS

International Search Report (Form PCT/ISA/210) issued Apr. 10, 2012, by the Japanese Patent Office as the International Searching Authority for International Application No. PCT/JP2012/053575. (2 pages).

Extended European Search Report issued Nov. 18, 2016, by the European Patent Office in corresponding European Patent Application No. 12746547.4 (7 pages).

* cited by examiner

SPUNBONDED NONWOVEN FABRICS

TECHNICAL FIELD

The present invention relates to spunbonded nonwoven fabrics formed of thermoplastic resin hollow fibers, preferably propylene polymer hollow fibers, which exhibit excellent strength, lightweight properties, flexibility, dispersion properties, shielding properties and forming properties and are suitable as sanitary materials.

BACKGROUND ART

Nonwoven fabrics of thermoplastic resin fibers, typically polypropylene nonwoven fabrics, have excellent breathability, flexibility and lightweight properties and have recently been used widely in various applications. Thus, the nonwoven fabrics require specific properties in accordance with the applications, and demands have been placed on the improvements of such properties.

In particular, disposable diapers have recently come to be heavily used in emerging countries, most typically China, due to population growth and have good market potentials in these countries. On the other hand, an increase in $CO_2$ emissions associated with the large consumption of disposable diapers is becoming a serious environmental problem. In order to suppress the worldwide increase in $CO_2$ emissions, plant-derived materials have been studied. However, the results are unsuccessful in terms of quality, costs and productivity. Meanwhile, manufacturers of disposable diapers have worked on saving $CO_2$ emissions by reducing the weight of nonwoven fabrics and packages, achieving only limited effects.

As an approach to substantially reducing the weight of nonwoven fabrics, nonwoven fabrics composed of hollow fibers have been proposed in various processes. For example, Patent Literature 1 proposes polypropylene nonwoven fabrics suitable as sanitary materials having a fiber diameter of not more than 20 μm and a hollowness of 5 to 70%. Table 1 in Patent Literature 1 describes a nonwoven fabric with a fiber diameter of 22.2 μm, a hollowness of 13% and a basis weight of 22.2 g/m².

Further, Patent Literature 2 proposes nonwoven fabrics that include continuous hollow fibers of a propylene polymer having a ratio (Mz/Mw) of Z average molecular weight (Mz) to weight average molecular weight (Mw) in the range from 1.5 to 1.9. Example 1 of this literature describes a spunbonded nonwoven fabric with a fiber diameter of 21.5 μm, a hollowness of 28.5% and a basis weight of 30 g/m².

Spunbonded nonwoven fabrics with excellent lightweight properties can be obtained according to the methods for the production of spunbonded nonwoven fabrics described in these patent literatures. In the case where the hollow fibers forming the spunbonded nonwoven fabrics are made finer to a fiber diameter of not more than 20 μm and a basis weight of not more than 20 g/m² in order to further reduce the weight of the spunbonded nonwoven fabrics, however, it has been found that the obtainable nonwoven fabrics are so nonuniform that they cannot be suitably used as sanitary materials.

CITATION LIST

Patent Literature

Patent Literature 1: U.S. Pat. No. 6,368,990
Patent Literature 2: WO 2010/024268

SUMMARY OF INVENTION

Technical Problem

It is an object of the present invention to obtain spunbonded nonwoven fabrics having excellent uniformity and exhibiting high strength and flexibility even in the case where the fiber diameter of hollow fibers forming the spunbonded nonwoven fabrics is reduced as well as the basis weight of the spunbonded nonwoven fabrics is reduced in order to obtain excellently lightweight spunbonded nonwoven fabrics. The present inventors carried out studies in order to achieve the object. As a result, the present inventors have found that spunbonded nonwoven fabrics with excellent uniformity can be obtained by controlling the C-axis orientation of propylene polymer hollow fibers to be not less than 0.85. The present invention has been accomplished based on the finding.

Solution to Problem

An aspect of the invention is directed to a spunbonded nonwoven fabric including hollow fibers of a propylene polymer, the hollow fibers satisfying the following requirements (a) to (c):
  (a) the C-axis orientation is at least 0.85,
  (b) the average fiber diameter is 5 to 20 μm, and
  (c) the hollowness is 5 to 30%.

Advantageous Effects of Invention

The spunbonded nonwoven fabrics according to the present invention exhibit excellent uniformity, high strength and flexibility even in the case where the fiber diameter of hollow fibers is reduced to 20 μm or less as well as where the basis weight is reduced. Sufficient strength can be ensured even if the basis weight is decreased to a lower level than conventional. Thus, the weight reduction of nonwoven fabrics is feasible.

In an embodiment, the spunbonded nonwoven fabric includes hollow fibers with an eccentric hollow. Because such hollow fibers are crimped, improvements in flexibility and bulkiness are obtained in addition to the above advantageous effects.

DESCRIPTION OF EMBODIMENTS

⟨Thermoplastic Resins⟩

Figure 1:
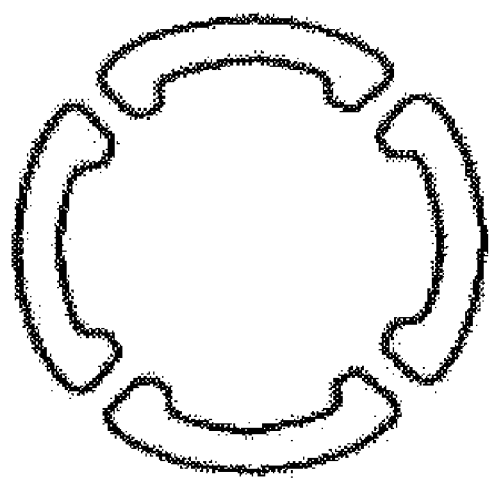
FIG. 1 is a view illustrating a configuration of nozzle pores used for the formation of hollow fibers according to the invention.

Hollow fibers constituting spunbonded nonwoven fabrics according to the invention are formed of thermoplastic resins. Various known thermoplastic resins may be used. Examples include homopolymers and copolymers of α-olefins such as ethylene, propylene, 1-butene, 1-hexene, 4-methyl-1-pentene and 1-octene. Specific examples include ethylene polymers such as high-pressure low-density polyethylenes, linear low-density polyethylenes (LLDPE) and high-density polyethylenes (HDPE); propylene polymers such as polypropylenes (propylene homopolymers), propylene/α-olefin random copolymers and propylene block copolymers; polyolefins such as poly(1-butene), poly(4-methyl-1-pentene), ethylene/propylene random copolymers, ethylene/1-butene random copolymers and propylene/1-butene random copolymers; polyesters (such as polyethylene terephthalates, polybutylene terephthalates and polyethylene naphthalates); polyamides (such as nylon-6, nylon-66 and poly(meta-xylene adipamide); polyvinyl chlorides, polyimides, ethylene/vinyl acetate copolymers, ethylene/vinyl acetate/vinyl alcohol copolymers, ethylene/(meth) acrylic acid copolymers, ethylene/acrylate/carbon monoxide copolymers, polyacrylonitriles, polycarbonates, polystyrenes and ionomers. Of these, ethylene polymers, propylene polymers, polyethylene terephthalates and polyamides are more preferable.

The above thermoplastic resins may be used singly, or two or more kinds of the thermoplastic resins may be used as a mixture.

Of the above thermoplastic resins, propylene polymers are particularly preferable from the viewpoints of spinning stability during spinning as well as stretch workability of nonwoven fabrics.

⟨Propylene Polymers⟩

The propylene polymer forming the hollow fibers of spunbonded nonwoven fabrics according to the invention is a homopolymer of propylene or a random copolymer (a propylene/α-olefin random copolymer) of propylene and one, or two or more kinds of α-olefins having 2 or more carbon atoms, and preferably 2 to 8 carbon atoms such as ethylene, 1-butene, 1-pentene, 1-hexene, 1-octene and 4-methyl-1-pentene. The propylene polymer usually has a melting point (Tm) of not less than 125° C., and preferably in the range from 125 to 165° C. The amount of the α-olefins copolymerized is not particularly limited as long as the obtainable propylene polymer exhibits a melting point (Tm) in the above range. However, the amount is usually not more than 10 mol %, and preferably not more than 6 mol %.

When a propylene/α-olefin random copolymer is used as the propylene polymer, it is preferable to use a propylene/α-olefin random copolymer having a melting point (Tm) of not more than 153° C., and more preferably in the range from 125 to 150° C.

The melt flow rate (MFR) (ASTM D-1238, 230° C., 2160 g load) of the propylene polymer in the invention is not particularly limited as long as the polymer can form spunbonded nonwoven fabrics. The melt flow rate, however, is usually in the range from 10 to 100 g/10 min, and preferably 20 to 70 g/10 min. If the MFR is less than 10 g/10 min, the propylene polymer tends to exhibit high melt viscosity and poor spinnability, possibly failing to form thin hollow fibers. If the melt flow rate of the propylene polymer exceeds 100 g/10 min, the obtainable spunbonded nonwoven fabric may exhibit poor properties such as tensile strength.

The propylene polymers in the invention may be blended with common additives or other polymers as required while still achieving the objects of the invention. Exemplary additives include antioxidants, weathering stabilizers, light stabilizers, antistatic agents, hydrophilic agents, antifogging agents, antiblocking agents, lubricants, nucleating agents and pigments.

⟨Spunbonded Nonwoven Fabrics⟩

A spunbonded nonwoven fabric according to the invention includes hollow fibers of the above propylene polymer, the hollow fibers having (a) a C-axis orientation of at least 0.85, preferably not less than 0.90, (b) an average fiber diameter of 5 to 20 μm, preferably 5 to 17 μm, and (c) a hollowness of 5 to 30%, preferably 10 to 30%, more preferably 14 to 30%.

If the fibers have a hollowness of less than 5%, the C-axis orientation becomes less than 0.85 and the uniformity of the obtainable spunbonded nonwoven fabric may be deteriorated.

The present invention provides that the hollowness is controlled to be in the range from 5 to 30% as well as the C-axis orientation to be not less than 0.85. This configuration advantageously ensures that nonwoven fabrics can be produced while the occurrence of resin masses (shots) is prevented even in the case where the output rate is increased to improve productivity while the amount of cooling air is relatively small.

If the average fiber diameter exceeds 20 μm, such fibers are excessively thick and will not be dispersed sufficiently. As a result, the obtainable spunbonded nonwoven fabric may be unsatisfactory in terms of uniformity even if the fibers achieve a C-axis orientation of not less than 0.85. Further, such a spunbonded nonwoven fabric is poor in flexibility and is not suitably used as sanitary materials.

The above average fiber diameter and hollowness ensure that the inventive spunbonded nonwoven fabrics exhibit excellent properties such as lightweight properties and tensile strength.

The hollow fibers forming the inventive spunbonded nonwoven fabrics may have an eccentric hollow. In the invention, such hollow fibers having an eccentric hollow (hereinafter, also referred to as "eccentric hollow fibers") are hollow fibers in which the center of the hollow is found at a different position from the center of the hollow fiber in a cross section of the fiber.

In the case where the inventive spunbonded nonwoven fabric is formed of the eccentric hollow fibers, the C-axis orientation (a) is not necessarily limited, but the average fiber diameter (b) is usually in the range from 5 to 50 μm, preferably 5 to 30 μm, more preferably 5 to 20 μm, and most preferably 5 to 17 μm. In a preferred embodiment, the eccentric hollow fibers may satisfy the aforementioned C-axis orientation (a) and hollowness (c).

When the inventive spunbonded nonwoven fabric is formed of eccentric hollow fibers, the hollow fibers are crimped. The term "crimped" means that the fibers have three or more crimps. The inventive spunbonded nonwoven fabric formed of such eccentric hollow fibers exhibit excellent flexibility and bulkiness because of the crimps of the hollow fibers.

The number of crimps of the inventive hollow fibers may be determined in accordance with JIS L 1015. The number of crimps is usually not less than 3, preferably not less than 5, and more preferably not less than 7 per 25 mm of the fiber. The upper limit is not particularly specified. Few crimps may fail to provide properties such as bulkiness which are attributed to the three dimensional helical structures of fibers.

The spunbonded nonwoven fabrics of the invention preferably have a basis weight in the range from 5 to 20 g/m$^2$, and more preferably 5 to 15 g/m$^2$. The spunbonded nonwoven fabrics having this basis weight exhibit excellent properties such as lightweight properties, flexibility and tensile strength.

The spunbonded nonwoven fabrics of the invention preferably have a uniformity (a degree of uniformity) in the range from 0.01 to 0.85, and more preferably 0.01 to 0.7. The spunbonded nonwoven fabrics having this uniformity exhibit excellent properties such as tensile strength and water resistance.

Depending on applications, the spunbonded nonwoven fabrics of the invention may be entangled by various known entangling methods, for example, by needle punching, water jetting or ultrasonicating or by partial thermal fusion bonding through hot embossing with an embossing roll or by blowing of hot air through the fibers. These entangling methods may be used singly, or a plurality of these methods may be used in combination.

When the spunbonded nonwoven fabrics are thermally fusion bonded by hot embossing, the emboss area percentage is usually in the range from 3 to 20%, preferably 3 to 10%, and the non-emboss unit area is not less than 0.5 mm$^2$, preferably in the range from 4 to 40 mm$^2$. The non-emboss unit area is the maximum area of a tetragon inscribed in bosses among the minimum units of non-embossing sections surrounded by bosses. These embossing configurations ensure that the obtainable spunbonded nonwoven fabrics exhibit excellent strength and flexibility.

In the case where the entangling treatment is carried out by needle punching, spunbonded nonwoven fabrics exhibiting excellent strength and flexibility may be obtained by using a known needle punching machine while controlling conditions such as needle density, needle type, needle depth and punch counts in accordance with the nature or properties of the fibers. In some cases, entanglement effects may be optimized by passing the spunbonded nonwoven fabrics through a plurality of needle punching machines.

In an embodiment, the spunbonded nonwoven fabric of the invention includes thermoplastic resin hollow fibers with an eccentric hollow.

Figure 3:
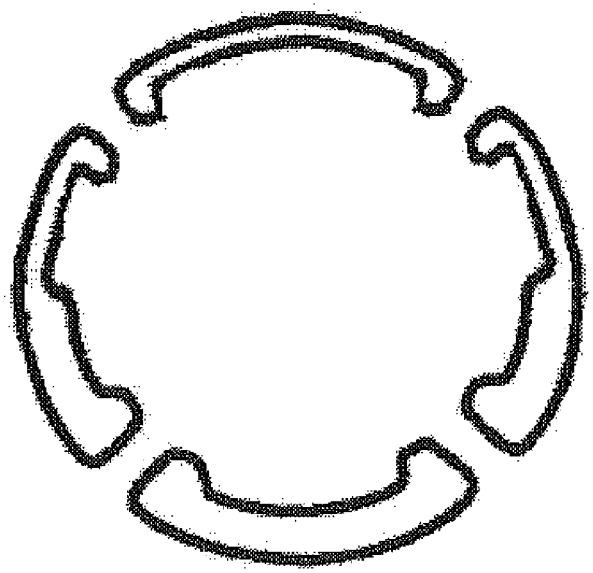
FIG. 3 is a view illustrating another configuration of nozzle pores used for the formation of hollow fibers according to the invention.

Such hollow fibers with an eccentric hollow according to the invention are eccentric hollow fibers obtained by spinning a thermoplastic resin as one component through a plurality of asymmetrically shaped slits of orifices (nozzles) such as those illustrated in FIG. 3. Such eccentric hollow fibers are distinguished from so-called eccentric conjugate hollow fibers obtained by spinning different kinds of thermoplastic resins from respective slits.

The phrase "thermoplastic resin as one component" means that a thermoplastic resin for making the fibers forms one component not only as an individual thermoplastic resin or as a mixture of two or more kinds of thermoplastic resins described above.

⟨Methods for Producing Spunbonded Nonwoven Fabrics⟩

The spunbonded nonwoven fabrics of the invention may be produced by closed spunbonding processes such as those disclosed in JP-A-S60 (1985)-155765, Japanese Patent No. 3442896 and Japanese Patent No. 3883818.

In detail, an exemplary process will be described. An apparatus for producing spunbonded nonwoven fabrics is used which includes a closed cooling chamber illustrated in FIG. 5 that is equipped with a spinneret (die) having a large number of orifices (nozzles) illustrated in FIG. 1 that are capable of forming hollow fibers cross-sectionally illustrated in FIG. 2. The propylene polymer is melt spun through the large number of orifices (nozzles), and the resultant continuous hollow fibers of the propylene polymer are cooled with cooling air introduced into the cooling chamber. The fibers are then passed through a narrow aisle (a drawing section) downstream from the cooling chamber in which the cooling air that has been used for cooling is utilized as drawing air. After being drawn (attenuated) with the drawing air, the continuous fibers are dispersed with a diffuser disposed downstream and are deposited onto a moving collection surface (a mesh belt).

Figure 4:
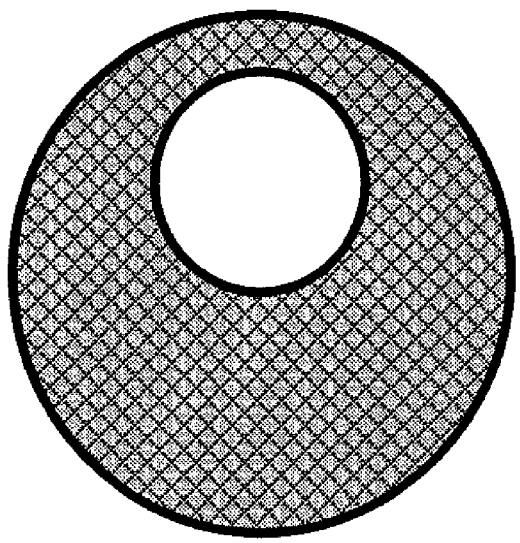
FIG. 4 is a view illustrating a cross section of a fiber extruded from the nozzle pores depicted in FIG. 3 during the formation of a spunbonded nonwoven fabric according to the invention.
Figure 5:
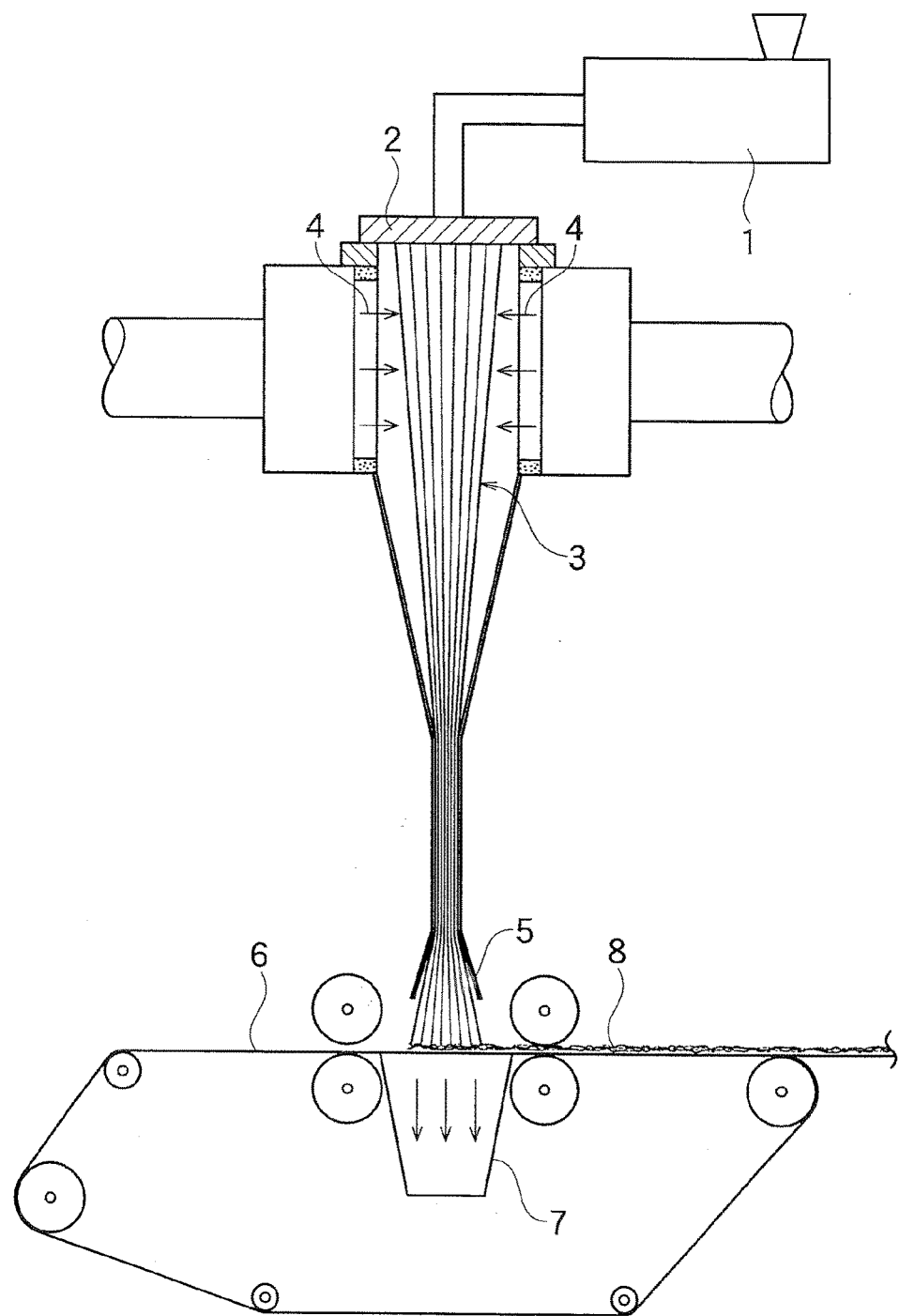
FIG. 5 is a schematic view illustrating an apparatus for producing spunbonded nonwoven fabrics used in Examples of the invention.

The production is also possible with an apparatus for producing spunbonded nonwoven fabrics which includes a closed cooling chamber illustrated in FIG. 5 that is equipped with a spinneret (die) having a large number of orifices (nozzles) illustrated in FIG. 3 that are capable of forming hollow fibers cross-sectionally illustrated in FIG. 4. In this case, the obtainable spunbonded nonwoven fabrics are composed of hollow fibers having an eccentric hollow.

The temperature for melting the propylene polymer is not particularly limited as long as the hollow fibers are sufficiently oriented about the C axis, but may be usually set at a temperature in the range from 180 to 280° C., preferably 190 to 270° C., and more preferably 200 to 260° C.

The temperature of the cooling air is not particularly limited as long as the propylene polymer is solidified at the temperature. However, the cooling air temperature is usually in the range from 5 to 50° C., preferably 10 to 40° C., and more preferably 15 to 30° C. The cooling air that has traveled to the diffuser functions as a dispersing medium for sufficiently dispersing the fibers. In order to ensure uniformity that is an advantageous effect achieved by the invention, the gas volume is usually in the range from 30 to 100 Nm$^3$/min/m, preferably 35 to 80 Nm$^3$/min/m, and more preferably 40 to 60 Nm$^3$/min/m. The velocity of the drawing air is usually in the range from 100 to 10,000 m/min, and preferably 500 to 10,000 m/min.

In order to obtain propylene polymer fibers with a hollow cross section having an average fiber diameter of 5 to 20 and a hollowness of 5 to 30%, in particular an average fiber diameter of 5 to 15 μm and a hollowness of 14 to 30%, it is preferable to use a spinneret provided with orifices (nozzles) with an outer diameter of 0.5 to 5.0 mm, a slit width of 0.05 to 0.5 mm, a number of slits of 2 to 10, preferably 3 to 6, an interval between slits, namely, a canal width of 0.04 to 0.15 mm, and a nozzle pore area of 0.1 to 0.5 mm$^2$. In order to obtain nonwoven fabrics having high uniformity that is an advantageous effect achieved by the invention, it is preferable to use a spinneret provided with orifices in which the value of the canal width divided by the nozzle pore area (canal width/nozzle pore area) is preferably not less than 0.35 mm$^{-1}$, and more preferably not less than 0.40 mm$^{-1}$.

Figure 2:
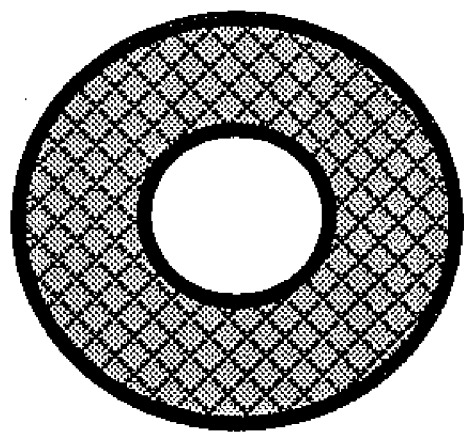
FIG. 2 is a view illustrating a cross section of a fiber extruded from the nozzle pores depicted in FIG. 1 during the formation of a spunbonded nonwoven fabric according to the invention.

In the invention, the canal width in the orifices is a width (an interval) between slits (nozzle pores) illustrated in, for example, FIG. 1 or FIG. 3 through which a melt such as the propylene polymer is extruded. The nozzle pore area is the total of the areas of all the slits (nozzle pores).

If the outer diameter of the orifices exceeds 5.0 mm, it may be difficult to obtain continuous fibers with a fiber diameter of not more than 20 μm. If the slit width of the orifices exceeds 0.5 mm, it may be difficult to obtain continuous fibers with a hollowness in excess of 5%. If the number of slits is less than 2, or is more than 10, it may be difficult to obtain continuous fibers with a hollowness in excess of 5%.

Even if conventional spunbonded nonwoven fabrics (spunbonded nonwoven fabrics of solid continuous fibers) are manufactured using a spunbonding apparatus equipped with a similar closed cooling device so as to obtain fiber diameters of not more than 20 μm, the obtained (solid) fibers do not have a C-axis orientation of not less than 0.85. On the other hand, even if hollow fibers with a hollowness of 5 to 30% are manufactured using a spunbonding apparatus equipped with an open cooling device, the C-axis orientation is as low as about 0.7 and the obtainable spunbonded nonwoven fabrics tend to be poor in uniformity.

《Spunbonded Nonwoven Fabric Laminate》

Other layers may be laminated to the inventive spunbonded nonwoven fabrics in accordance with various applications. Such additional layers laminated to the spunbonded nonwoven fabrics are not particularly limited, and various kinds of layers may be laminated depending on applications.

Specific examples include knitted fabrics, woven fabrics, nonwoven fabrics and films. Such additional layers may be laminated (stacked/bonded) to the spunbonded nonwoven fabrics of the invention by any known methods, for example, thermal fusion bonding methods such as hot embossing and ultrasonic fusion bonding, mechanical entangling methods such as needle punching and water jetting, bonding methods with adhesives such as hot melt adhesives and urethane adhesives, and extrusion lamination.

The nonwoven fabrics laminated to the spunbonded nonwoven fabrics of the invention may be any known nonwoven fabrics such as usual spunbonded nonwoven fabrics, meltblown nonwoven fabrics, wet nonwoven fabrics, dry nonwoven fabrics, dry pulp nonwoven fabrics, flash-spun nonwoven fabrics and split-fiber nonwoven fabrics.

The films laminated to the spunbonded nonwoven fabrics of the invention are preferably breathable (moisture permeable) films in order to take advantage of the breathability, flexibility and lightweight properties that are characteristics of the inventive spunbonded nonwoven fabrics. Various known breathable films may be used, with examples including moisture permeable films of thermoplastic elastomers such as polyurethane elastomers, polyester elastomers and polyamide elastomers; and porous films obtained by drawing thermoplastic resin films containing inorganic or organic fine particles to create pores in the films. Preferred thermoplastic resins used for the porous films are polyolefins such as high-pressure low-density polyethylenes, linear low-density polyethylenes (LLDPE), high-density polyethylenes, polypropylenes, polypropylene random copolymers and compositions thereof.

Laminates including breathable films can be cloth-like composite materials that maintain flexibility inherent to the inventive spunbonded nonwoven fabrics as well as exhibit very high water resistance.

The inventive spunbonded nonwoven fabric and a meltblown nonwoven fabric may be laminated together by any method without limitation as long as the method is capable of combining the two into a laminate. Examples of such methods include a method in which meltblown fibers are directly deposited onto the spunbonded nonwoven fabric to form a meltblown nonwoven fabric and the spunbonded nonwoven fabric and the meltblown nonwoven fabric are fusion bonded with each other; a method in which the spunbonded nonwoven fabric and a meltblown nonwoven fabric are placed one on top of the other and the two nonwoven fabrics are fusion bonded with each other by thermal pressing; and a method in which the spunbonded nonwoven fabric and a meltblown nonwoven fabric are bonded together via an adhesive such as a hot melt adhesive or a solvent adhesive.

A meltblown nonwoven fabric may be directly formed on the spunbonded nonwoven fabric by a meltblowing method in which a thermoplastic resin melt is sprayed onto a surface of the spunbonded nonwoven fabric to deposit the fibers. During meltblowing, air is suctioned from the backside of the spunbonded nonwoven fabric so as to attract meltblown fibers sprayed onto the front side. In this manner, the spunbonded nonwoven fabric is combined with a meltblown nonwoven fabric simultaneously with the deposition of fibers, resulting in a laminated nonwoven fabric having a spunbonded nonwoven fabric layer and a meltblown nonwoven fabric layer. In the case where the attachment between the two nonwoven fabrics is insufficient, the laminate may be sufficiently united by, for example, thermal pressing with embossing rolls.

Exemplary methods for thermally fusion bonding the spunbonded nonwoven fabric with a meltblown nonwoven fabric include a method in which the spunbonded nonwoven fabric and a meltblown nonwoven fabric are fusion bonded at the entirety of their surfaces in contact with each other, and a method in which the spunbonded nonwoven fabric and a meltblown nonwoven fabric are fusion bonded at portions of their surfaces in contact with each other. In the present invention, it is preferable that the spunbonded nonwoven fabric and a meltblown nonwoven fabric be fusion bonded together by hot embossing. In this case, the fusion bonding area is 3 to 30%, preferably 3 to 20%, and more preferably 3 to 10% of the area of contact between the spunbonded nonwoven fabric and the meltblown nonwoven fabric. This fusion bonding area ensures that the laminated nonwoven fabric exhibits excellent balance between peel strength and flexibility.

Examples of the hot melt adhesives used to bond the spunbonded nonwoven fabrics and meltblown nonwoven fabrics include resin adhesives such as vinyl acetate adhesives and polyvinyl alcohol adhesives, and rubber adhesives such as styrene/butadiene adhesives and styrene/isoprene adhesives. Examples of the solvent adhesives include organic solvent or aqueous emulsion adhesives based on rubber adhesives such as styrene/butadiene adhesives, styrene/isoprene adhesives and urethane adhesives, and adhesives based on resin such as vinyl acetate and vinyl chloride. Of the adhesives, rubber hot melt adhesives such as styrene/isoprene adhesives and styrene/butadiene adhesives are preferable because the characteristic texture of the spunbonded nonwoven fabrics is not deteriorated.

《Meltblown Nonwoven Fabrics》

A preferred meltblown nonwoven fabric laminated to the inventive spunbonded nonwoven fabric includes polyolefin fibers and has (i) an average fiber diameter of not more than 2 μm, (ii) a coefficient of variation of fiber diameter (CV) of not more than 60%, preferably not more than 50%, and (iii) a number of fusion bonding per 100 fibers of not more than 15, preferably not more than 12, more preferably not more than 10.

Another preferred meltblown nonwoven fabric laminated to the inventive spunbonded nonwoven fabric includes propylene polymer fibers and has (i) an average fiber diameter of not more than 2 μm, (ii) a coefficient of variation of fiber diameter (CV) of not more than 60%, preferably not more than 50%, and (iv) an α-crystal fraction of less than 0.9.

Meltblown nonwoven fabrics having the above properties may be produced by, for example, a method described in PCT/JP2011/078082.

《Applications》

The spunbonded nonwoven fabrics obtained according to the present invention, and the nonwoven fabric laminate including the inventive spunbonded nonwoven fabrics may be used in various applications.

For example, these nonwoven fabrics may be widely used in medical materials, industrial materials, civil engineering and building materials, agricultural and gardening materials, and daily life materials, in detail, surgical gowns, bandages, bedclothes such as bed sheets and pillowcases, and substrates for carpets and artificial leathers Because the spunbonded nonwoven fabrics or the nonwoven fabric laminate according to the invention are lightweight and have good flexibility and texture, they may be particularly suitably used in disposable diapers, solid gather sheets and sanitary napkins.

⟨Solid Gather Sheets⟩

Disposable diapers according to the invention utilize the inventive spunbonded nonwoven fabrics, or the nonwoven fabric laminates including the inventive spunbonded nonwoven fabrics. The inventive nonwoven fabrics can form members for solid gathers in products such as disposable diapers and sanitary napkins.

Solid gathers are required to exhibit excellent breathability, prevent the leakage of loose stool, and have comfortable touch. In view of these requirements, the inventive spunbonded nonwoven fabrics, or the nonwoven fabric laminates including the inventive spunbonded nonwoven fabrics are suitably used in such applications.

⟨Back Sheets⟩

The disposable diapers according to the invention utilize the inventive spunbonded nonwoven fabrics, or the nonwoven fabric laminates including the inventive spunbonded nonwoven fabrics. The inventive nonwoven fabrics can form members for back sheets in products such as disposable diapers and sanitary napkins.

Back sheets are required to exhibit excellent breathability, be hollow to provide high shielding properties, and have comfortable touch. In view of these requirements, the inventive spunbonded nonwoven fabrics, or the nonwoven fabric laminates including the inventive spunbonded nonwoven fabrics are suitably used in such applications.

EXAMPLES

The present invention will be described in detail hereinbelow based on examples without limiting the scope of the invention to such examples.

In examples and comparative examples, properties and characteristics were measured by the following methods.

(1) Measurement of C-Axis Orientation

A wide-angle X-ray diffractometer (RINT 2550 manufactured by Rigaku Corporation, attachment: fiber sample table, X-ray source: CuKα, output: 40 kV 370 mA, detector: scintillation counter) was used. Sample fibers were arranged along a fiber axial direction and were fixed on the sample holder. Intensities were measured which indicated the azimuths of a peak of a crystal planes [(110) planes], and an azimuthal distribution curve (an X-ray interference diagram) was obtained. Based on the half-width (α) of the peak, the orientation (the C-axis orientation) of the hollow fibers with respect to the fiber axial direction was calculated according to the following equation.

Orientation $(F)=(180°-α)/180°$ (α is the half-width of the peak in the azimuthal distribution curve.)

(2) Fiber Diameter (μm)

A spunbonded nonwoven fabric was observed with an optical microscope (ECLIPSE E-400 manufactured by Nikon). Fiber diameters were measured with respect to randomly selected 100 filaments forming the spunbonded nonwoven fabric on the screen. The average was obtained as the fiber diameter of the nonwoven fabric.

(3) Fineness [d]

The fineness of the spunbonded nonwoven fabric was calculated according to the following equation.

Fineness $[d]=0.00225×π×ρ[g/cm^3]×D^2[μm]×(1-\text{hollowness }[\%])$

Here, ρ [g/cm$^3$] is the melt density of the resin at the service temperature, and D is the fiber diameter.

(4) Single Filament Strength [gf/d]

In accordance with JIS L 1905 (7.5.1 method), 60 filaments were collected and subjected to a tensile test in a thermostatic chamber at a temperature of 20±2° C. and a humidity of 65±2% in accordance with JIS Z 8703 (standard conditions at testing sites) using a tensile tester (Instron 5564 manufactured by Instron Japan Co., Ltd.) with a chuck distance of 20 mm and at a stress rate of 20 mm/min, thereby determining the tensile loads of the 60 filament test pieces. The average of the maximum loads was obtained as the single filament strength.

(5) Hollowness [%]

A spunbonded nonwoven fabric was buried in an epoxy resin and was cut with a microtome to give a sample piece. The sample piece was observed with an electron microscope (scanning electron microscope S-3500N manufactured by Hitachi, Ltd.). In the obtained cross sectional image of the fibers, the cross sectional area of the entire fiber and that of the hollow were obtained. The hollowness was calculated from the following equation.

Hollowness $[\%]=(\text{cross sectional area of hollow}/\text{cross sectional area of entire fiber})×100$ An average of 100 fibers was obtained as the hollowness.

(6) Flexibility (Flexural rigidity) [45° Cantilever Method]

In accordance with JIS L 1096 (6.19.1 A method), a spunbonded nonwoven fabric was cut in a thermostatic chamber at a temperature of 20±2° C. and a humidity of 65±2% in accordance with JIS Z 8703 (standard conditions at testing sites) to give 5 test pieces, 20 mm×150 mm, along each of the machine direction (MD) and the cross direction (CD). Each test piece was placed on a horizontal, smooth-surface table having a 45° slope surface, with the shorter side of the test piece aligned at the scale baseline. Next, the test piece was manually slid slowly toward the slope surface. When the central point at one end of the test piece touched the slope surface, the length by which the other end had moved was measured by reading the scales. The flexibility (flexural rigidity) was indicated in length (mm) of the movement of the test piece. Each of the 5 test pieces was tested with respect to both the front and back sides. The average in machine direction (MD) and that in cross direction (CD) were obtained.

(7) Tensile Strength (Strength)

In accordance with JIS L 1906 (6.12.1 A method), a nonwoven fabric was cut in a thermostatic chamber at a temperature of 20±2° C. and a humidity of 65±2% in accordance with JIS Z 8703 (standard conditions at testing sites) to give 3 test pieces 25 cm in machine direction (MD) and 2.5 cm in cross direction (CD). The test pieces were subjected to a tensile test with a tensile tester (Instron 5564 manufactured by Instron Japan Co., Ltd.) with a chuck distance of 30 mm and at a stress rate of 30 mm/min to determine the tensile loads of the 3 test pieces. The average of the maximum loads was obtained as the tensile strength.

(8) Uniformity (Degree of Uniformity)

A nonwoven fabric was cut in a thermostatic chamber at a temperature of 20±2° C. and a humidity of 65±2% in accordance with JIS Z 8703 (standard conditions at testing sites) to give a test piece 25 cm in machine direction (MD) and 20 cm in cross direction (CD). The weight thereof was obtained and a basis weight was calculated as an average basis weight (g/m²). Next, this nonwoven fabric was punched with a punch (a punching jig) 13 mm in inner diameter at randomly selected 15 points in the MD and at randomly selected 10 points in the CD. In this manner, a total of 150 test pieces were sampled from the nonwoven fabric. The weights of all the test pieces were measured. Of the test pieces, the 5 heaviest test pieces and the 20 lightest test pieces were selected as thicker portions and thinner portions, respectively. The respective averages were obtained, and the degree of uniformity was determined from the following equation.

Degree of uniformity=(average basis weight of thicker portions—average basis weight of thinner portions)/average basis weight The nonwoven fabric is more uniform with decreasing degree of uniformity.

(9) FUKURAMI Value ⟨Evaluation of Bulkiness⟩

A nonwoven fabric was tested with KES-FB system manufactured by KATO TECH CO., LTD. in terms of tension, shear, compression, surface friction and bending under highly sensitive conditions for knitted fabrics. The measurement results were analyzed under knitted underwear (summer) conditions to obtain a FUKURAMI value. The larger the FUKURAMI value, the bulkier and the more flexible.

(10) Water Pressure Resistance (mm Aqua)

In accordance with JIS L 1092 (A method), a nonwoven fabric laminate as a water treatment filter was cut in a thermostatic chamber at a temperature of 20±2° C. and a humidity of 65±2% in accordance with JIS Z 8703 (standard conditions at testing sites) to give 10 test pieces, each 15×15 cm. The test pieces were tested using a water pressure resistance tester to determine the pressure which caused water leakage. The results were averaged.

(11) Number of Crimps

The number of crimps was counted in accordance with JIS L 1015.

Compartment lines having a spatial distance of 25 mm were drawn on smooth and gloss paper.

Next, before a nonwoven fabric of continuous fibers was thermally pressed with embossing rolls, fibers were carefully collected from the nonwoven fabric while paying attention not to relax the crimps. Both ends of each collected fiber were bonded onto the paper via an adhesive while allowing 25±5% looseness relative to the spatial distance. Each of such sample fibers was analyzed in the following manner to count the crimps. The individual fiber was attached to chucks of a crimp tester. After the paper was cut, an initial load (0.18 mN×tex) was applied to the sample and the distance between the chucks (the spatial distance) (mm) was read. In that state, the crimps were counted, thereby determining the number of crimps per 25 mm. The crimps were counted in such a manner that all the peaks and valleys were counted and the sum was halved.

The above measurement was performed with respect to 20 fibers. The average was rounded to one decimal place, thus determining the number of crimps of eccentric hollow fibers. The number of crimps was measured under conditions in accordance with JIS Z 8703 (standard conditions at testing sites), namely, in a thermostatic chamber at a temperature of 20±2° C. and a humidity of 65±2%.

Example 1

A propylene homopolymer (PP-1) was used which had a MFR of 60 g/10 min as measured under 2160 g load at 230° C. This propylene polymer was molten in an extruder (screw diameter: 75 mm) at a forming temperature of 240° C. A nonwoven fabric production apparatus (a spunbonding apparatus, the length of the collection surface in the direction perpendicular to the machine direction: 320 mm) illustrated in FIG. 5 was equipped with a spinning spinneret having nozzles at pitches of 4.5 mm in the longitudinal direction and 4.0 mm in the traverse direction as well as having a canal width/pore area of 0.41 mm$^{-1}$. This spinneret had an orifice configuration illustrated in FIG. 1 and was capable of forming hollow fibers with a cross section illustrated in FIG. 2. The PP-1 melt was spun at an output rate per orifice of 0.52 g/min and a filament speed of 4367 m/min while blowing cooling air (25° C., flow rate: 42 Nm³/min/m). The fibers were deposited onto a collection belt, and the web was thermally compressed with embossing rolls (emboss area percentage: 18%, embossing temperature: 132° C.) to give a spunbonded nonwoven fabric having a basis weight of 15 g/m².

In FIG. 5, the reference signs are extruder 1, spinning spinneret 2, hollow fibers 3, cooling air 4, diffuser 5, collection device 6, suction device 7, and web (spunbonded nonwoven fabric) 8.

The hollow fibers and the spunbonded nonwoven fabric obtained were tested to evaluate the C-axis orientation, the average fiber diameter, the fineness, the single filament strength, the hollowness and the number of crimps of the hollow fibers, as well as the flexural rigidity, the tensile strength and the FUKURAMI value of the spunbonded nonwoven fabric. The results are described in Table 1.

Example 2

A spunbonded nonwoven fabric having a basis weight of 15 g/m² was obtained in the same manner as in Example 1, except that the PP-1 was spun at an output rate per orifice of 0.6 g/min and a filament speed of 4338 m/min.

The filaments and the spunbonded nonwoven fabric obtained were tested to evaluate the C-axis orientation, the average fiber diameter, the fineness, the single filament strength, the hollowness and the number of crimps of the hollow fibers, as well as the flexural rigidity, the tensile strength and the FUKURAMI value of the spunbonded nonwoven fabric. The results are described in Table 1.

Example 3

A spunbonded nonwoven fabric having a basis weight of 15 g/m² was obtained in the same manner as in Example 2, except that the forming temperature in the extruder (screw diameter: 75 mm) was changed to 220° C. and the melt was spun at a filament speed of 3013 m/min.

The filaments and the spunbonded nonwoven fabric obtained were tested to evaluate the C-axis orientation, the average fiber diameter, the fineness, the single filament strength, the hollowness and the number of crimps of the hollow fibers, as well as the flexural rigidity, the tensile strength and the FUKURAMI value of the spunbonded nonwoven fabric. The results are described in Table 1.

Example 4

⟨Production of Spunbonded Nonwoven Fabric⟩

A spunbonded nonwoven fabric was produced in the same manner as in Example 2, except that the basis weight of the spunbonded nonwoven fabric was changed to 6.15 g/m².

⟨Production of Nonwoven Fabric Laminate⟩

A propylene homopolymer (PP-2, MFR: 850 g/10 min, melting point: 159° C.) was supplied to a die of a meltblowing apparatus. The die temperature was set to 280° C. The polymer was extruded through meltblowing nozzles (diameter: 0.32 mm, pore to pore distance in the nozzles: 0.20 mm) at an output rate per nozzle orifice of 0.52 g/min while simultaneously blowing high-temperature high-speed air (280° C., 600 m³/hr) from both sides of the nozzles. The DCD (the die to collector distance) was 120 mm. In this manner, a meltblown nonwoven fabric having a basis weight of 0.7 g/m² was deposited onto one surface of the spunbonded nonwoven fabric obtained above, thereby producing a laminate including the spunbonded nonwoven fabric and the meltblown nonwoven fabric. Next, a spunbonded nonwoven fabric was laminated onto the meltblown nonwoven fabric under the same conditions as described above. Thus, a nonwoven fabric laminate having a total basis weight of 13.0 g/m² (spunbonded nonwoven fabric/meltblown nonwoven fabric/spunbonded nonwoven fabric=6.15/0.7/6.15 g/m²) was obtained.

The nonwoven fabric laminate obtained was tested to evaluate the C-axis orientation, the average fiber diameter, the fineness, the single filament strength, the hollowness and the number of crimps of the hollow fibers, as well as the flexural rigidity, the tensile strength and the water pressure resistance of the nonwoven fabric laminate. The results are described in Table 1.

Example 5

A nonwoven fabric laminate having a total basis weight of 13.0 g/m² (spunbonded nonwoven fabric/meltblown nonwoven fabric/spunbonded nonwoven fabric=6.15/0.7/6.15 g/m²) was obtained in the same manner as in Example 4, except that the meltblown nonwoven fabric was produced in such a manner that the extruded fibers were cooled and dispersed with cooling air (temperature 15° C., air volume: 6000 m³/hr).

The nonwoven fabric laminate obtained was tested to evaluate the C-axis orientation, the average fiber diameter, the fineness, the single filament strength, the hollowness and the number of crimps of the hollow fibers, as well as the flexural rigidity, the tensile strength and the water pressure resistance of the nonwoven fabric laminate. The results are described in Table 1.

Example 6

A spunbonded nonwoven fabric having a basis weight of 15 g/m² was obtained in the same manner as in Example 2, except that a propylene/α-olefin random copolymer (PP-3) was used as the propylene polymer which had a MFR of 60 g/10 min as measured under 2160 g load at 230° C. and a melting point of 143° C., as well as that this polymer was molten in the extruder (screw diameter: 75 mm) at a forming temperature of 220° C. and was spun at a filament speed of 3013 m/min onto the collection belt, and the web was thermally compressed with embossing rolls (emboss area percentage: 18%, embossing temperature: 115° C.).

The hollow fibers and the spunbonded nonwoven fabric obtained were tested to evaluate the C-axis orientation, the average fiber diameter, the fineness, the single filament strength, the hollowness and the number of crimps of the hollow fibers, as well as the flexural rigidity, the tensile strength and the FUKURAMI value of the spunbonded nonwoven fabric. The results are described in Table 1.

Example 7

A spunbonded nonwoven fabric having a basis weight of 15 g/m² was obtained in the same manner as in Example 2, except that the spinning spinneret used in Example 2 was replaced by a spinning spinneret with a canal width/pore area of 0.41 mm⁻¹ which had an orifice configuration illustrated in FIG. 3 and was capable of forming eccentric hollow fibers with a cross section illustrated in FIG. 4, as well as that the melt was spun at a filament speed of 4390 m/min.

The filaments and the spunbonded nonwoven fabric obtained were tested to evaluate the C-axis orientation, the average fiber diameter, the fineness, the single filament strength, the hollowness and the number of crimps of the hollow fibers, as well as the flexural rigidity, the tensile strength and the FUKURAMI value of the spunbonded nonwoven fabric. The results are described in Table 1.

Example 8

A spunbonded nonwoven fabric having a basis weight of 15 g/m² was obtained in the same manner as in Example 6, except that the spinning spinneret used in Example 6 was replaced by a spinning spinneret with a canal width/pore area of 0.41 mm⁻¹ which had an orifice configuration illustrated in FIG. 3 and was capable of forming eccentric hollow fibers with a cross section illustrated in FIG. 4, as well as that the melt was spun at a filament speed of 3048 m/min.

The filaments and the spunbonded nonwoven fabric obtained were tested to evaluate the C-axis orientation, the average fiber diameter, the fineness, the single filament strength, the hollowness and the number of crimps of the hollow fibers, as well as the flexural rigidity, the tensile strength and the FUKURAMI value of the spunbonded nonwoven fabric. The results are described in Table 1.

TABLE 1

| | | | Ex. 1 | Ex. 2 | Ex. 3 | Ex. 4 | Ex. 5 | Ex. 6 | Ex. 7 | Ex. 8 |
|---|---|---|---|---|---|---|---|---|---|---|
| Nozzles | Nozzle type | | Hollow | Hollow | Hollow | Hollow | Hollow | Hollow | Eccentric hollow | Eccentric hollow |
| | Canal width/pore area | mm⁻¹ | 0.41 | 0.41 | 0.41 | 0.41 | 0.41 | 0.41 | 0.41 | 0.41 |
| Materials | Kind | | PP-1 | PP-1 | PP-1 | PP-1 | PP-1 | PP-3 | PP-3 | PP-3 |
| Fibers | Fiber diameter | μm | 14 | 15 | 18 | 15 | 15 | 18 | 15 | 18 |
| | Fineness | d | 1.1 | 1.2 | 1.8 | 1.2 | 1.2 | 1.8 | 1.2 | 1.8 |
| | Hollowness | % | 15 | 14 | 14 | 14 | 14 | 14 | 15 | 15 |
| | Orientation | — | 0.93 | 0.89 | 0.92 | 0.89 | 0.89 | 0.9 | 0.91 | 0.88 |
| | Single filament strength | gf/d | 1.8 | 1.9 | 2.0 | 1.9 | 1.9 | 2.2 | 2.0 | 2.2 |
| | Number of crimps | Crimps/25 mm | 0 | 0 | 0 | 0 | 0 | 0 | 5.3 | 7.5 |

TABLE 1-continued

|  |  |  |  | Ex. 1 | Ex. 2 | Ex. 3 | Ex. 4 | Ex. 5 | Ex. 6 | Ex. 7 | Ex. 8 |
|---|---|---|---|---|---|---|---|---|---|---|---|
| Nonwoven fabrics | Basis weight | Total | g/m² | 15 | 15 | 15 | 13 | 13 | 15 | 15 | 15 |
|  |  | SB | g/m | 15 | 15 | 15 | 12.3 | 12.3 | 15 | 15 | 15 |
|  |  | MB | g/m² | 0 | 0 | 0 | 0.7 | 0.7 | 0 | 0 | 0 |
|  | Degree of uniformity |  | — | 0.59 | 0.65 | 0.63 | 0.71 | 0.71 | 0.68 | 0.66 | 0.71 |
|  | Strength | MD | N/25 mm | 27.5 | 26.6 | 24.1 | 23.1 | 23.5 | 16.2 | 24.9 | 16.8 |
|  |  | CD | N/25 mm | 7.1 | 6.3 | 6.1 | 5.2 | 5.3 | 5.1 | 5.8 | 5.6 |
|  | Flexural rigidity | MD | mm | 45 | 46 | 52 | 53 | 50 | 35 | 38 | 26 |
|  |  | CD | mm | 19 | 20 | 19 | 24 | 21 | 19 | 18 | 13 |
|  | Water pressure resistance |  | mm Aqua | — | — | — | 173 | 202 | — | — | — |
|  | KES |  | FUKURAMI value | 2.71 | 2.68 | 2.01 | — | — | 5.48 | 4.43 | 8.82 |

Comparative Example 1

A spunbonded nonwoven fabric having a basis weight of 15 g/m² was obtained in the same manner as in Example 1, except that the spinning spinneret for hollow fiber production used in Example 1 was replaced by a spinning spinneret with circular pores 0.6 mm in diameter (for solid fiber production), as well as that the melt was spun at a filament speed of 4283 m/min.

The filaments and the spunbonded nonwoven fabric obtained were tested to evaluate the C-axis orientation, the average fiber diameter, the fineness, the single filament strength and the number of crimps of the solid fibers, as well as the flexural rigidity, the tensile strength and the FUKURAMI value of the spunbonded nonwoven fabric. The results are described in Table 2.

Comparative Example 2

A spunbonded nonwoven fabric having a basis weight of 15 g/m² was obtained in the same manner as in Example 2, except that the polymer was molten in the extruder (screw diameter: 75 mm) at a forming temperature of 260° C. and the melt was spun at a filament speed of 4100 m/min while blowing cooling air (25° C., flow rate: 35 Nm³/min/m).

The filaments and the spunbonded nonwoven fabric obtained were tested to evaluate the C-axis orientation, the average fiber diameter, the fineness, the single filament strength, the hollowness and the number of crimps of the hollow fibers, as well as the flexural rigidity, the tensile strength and the FUKURAMI value of the spunbonded nonwoven fabric. The results are described in Table 2.

Comparative Example 3

A spunbonded nonwoven fabric having a basis weight of 15 g/m² was obtained by a spunbonding method in the same manner as in Comparative Example 2, except that the polymer was molten in the extruder (screw diameter: 75 mm) at a forming temperature of 200° C. and the melt was spun at a filament speed of 2296 m/min.

The filaments and the spunbonded nonwoven fabric obtained were tested to evaluate the C-axis orientation, the average fiber diameter, the fineness, the single filament strength, the hollowness and the number of crimps of the hollow fibers, as well as the flexural rigidity, the tensile strength and the FUKURAMI value of the spunbonded nonwoven fabric. The results are described in Table 2.

Comparative Example 4

Figure 6:
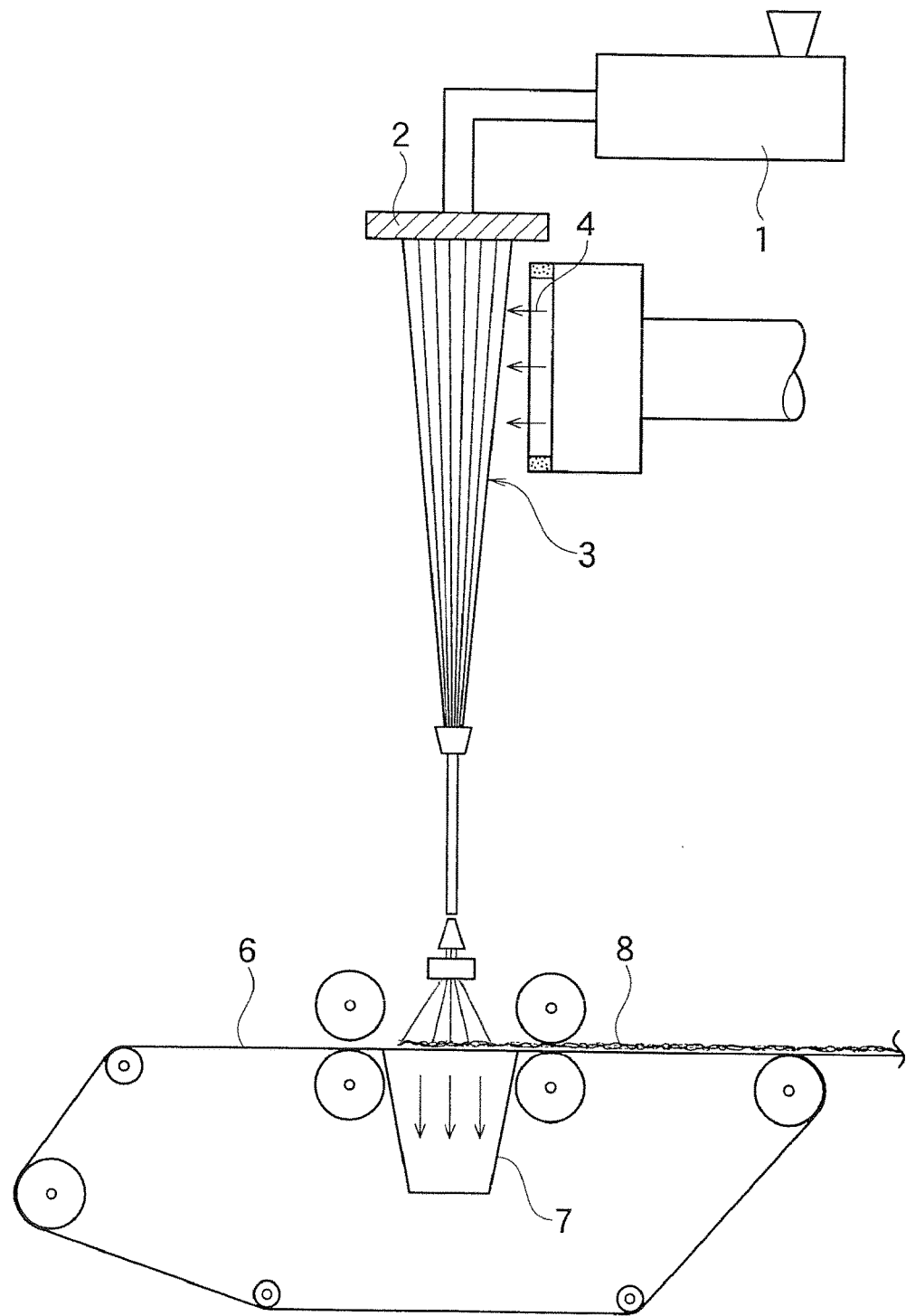
FIG. 6 is a schematic view illustrating an apparatus for producing spunbonded nonwoven fabrics used in Comparative Examples of the invention.

A spunbonded nonwoven fabric having a basis weight of 15 g/m² was obtained in the same manner as in Example 1, except that an open nonwoven fabric production apparatus (an open spunbonding apparatus, the length of the collection surface in the direction perpendicular to the machine direction: 320 mm) illustrated in FIG. 6 was used.

In FIG. 6, the reference signs are extruder 1, spinning spinneret 2, hollow fibers 3, cooling air 4, collection device 6, suction device 7, and web (spunbonded nonwoven fabric) 8.

The filaments and the spunbonded nonwoven fabric obtained were tested to evaluate the C-axis orientation, the average fiber diameter, the fineness, the single filament strength, the hollowness and the number of crimps of the hollow fibers, as well as the flexural rigidity, the tensile strength and the FUKURAMI value of the spunbonded nonwoven fabric. The results are described in Table 2.

Comparative Example 5

A spunbonded nonwoven fabric having a basis weight of 15 g/m² was obtained in the same manner as in Comparative Example 4, except that the spinning spinneret was replaced by a spinning spinneret with circular pores 0.6 mm in diameter (for solid fiber production), as well as that the melt was spun at a filament speed of 3731 m/min.

The filaments and the spunbonded nonwoven fabric obtained were tested to evaluate the C-axis orientation, the average fiber diameter, the fineness, the single filament strength and the number of crimps of the solid fibers, as well as the flexural rigidity, the tensile strength and the FUKURAMI value of the spunbonded nonwoven fabric. The results are described in Table 2.

Comparative Example 6

A spunbonded nonwoven fabric having a basis weight of 15 g/m² was obtained in the same manner as in Example 6, except that the spinning spinneret for hollow fiber production used in Example 6 was replaced by a spinning spinneret with circular pores 0.6 mm in diameter (for solid fiber production), as well as that the melt was spun at a filament speed of 2591 m/min.

The filaments and the spunbonded nonwoven fabric obtained were tested to evaluate the C-axis orientation, the average fiber diameter, the fineness, the single filament strength and the number of crimps of the solid fibers, as well as the flexural rigidity, the tensile strength and the FUKURAMI value of the spunbonded nonwoven fabric. The results are described in Table 2.

Comparative Example 7

A spunbonded nonwoven fabric having a basis weight of 15 g/m² was obtained in the same manner as in Example 2, except that the spinning spinneret used in Example 2 was replaced by a spinning spinneret for hollow fiber production as illustrated in FIG. 1 which had a canal width/pore area of 0.28 mm$^{-1}$, as well as that the melt was spun at a filament speed of 3807 m/min.

The filaments and the spunbonded nonwoven fabric obtained were tested to evaluate the C-axis orientation, the average fiber diameter, the fineness, the single filament strength, the hollowness and the number of crimps of the hollow fibers, as well as the flexural rigidity, the tensile strength and the FUKURAMI value of the spunbonded nonwoven fabric. The results are described in Table 2.

Comparative Example 8

A nonwoven fabric laminate having a total basis weight of 13.0 g/m$^2$ (spunbonded nonwoven fabric/meltblown nonwoven fabric/spunbonded nonwoven fabric=6.15/0.7/6.15 g/m$^2$) was obtained in the same manner as in Example 4, except that the spinning spinneret for hollow fiber production used in Example 4 was replaced by a spinning spinneret with circular pores 0.6 mm in diameter (for solid fiber production), as well as that the melt was spun at a filament speed of 2591 m/min.

The nonwoven fabric laminate obtained was tested to evaluate the C-axis orientation, the average fiber diameter, the fineness, the single filament strength and the number of crimps of the solid fibers, as well as the flexural rigidity, the tensile strength and the water pressure resistance of the nonwoven fabric laminate. The results are described in Table 2.

bedclothes including bed sheets and pillowcases, and substrates for carpets and artificial leathers.

The nonwoven fabric laminates including the inventive spunbonded nonwoven fabrics are lightweight, and also have flexibility and good texture. Thus, such nonwoven fabric laminates may be particularly suitably used in sanitary materials such as disposable diapers, solid gather sheets and sanitary napkins.

REFERENCE SIGNS LIST

1 . . . EXTRUDER
2 . . . SPINNING SPINNERET
3 . . . HOLLOW FIBERS
4 . . . COOLING AIR
5 . . . DIFFUSER
6 . . . COLLECTION DEVICE
7 . . . SUCTION DEVICE
8 . . . SPUNBONDED NONWOVEN FABRIC

The invention claimed is:

1. A spunbonded nonwoven fabric comprising hollow fibers of a propylene polymer, the hollow fibers satisfying the following requirements (a) to (c):
   (a) the C-axis orientation is at least 0.85,
   (b) the average fiber diameter is 5 to 20 μm, and
   (c) the hollowness is 5 to 30%.

2. The spunbonded nonwoven fabric according to claim 1, wherein (d) the basis weight is 5 to 20 g/m$^2$.

3. The spunbonded nonwoven fabric according to claim 1, wherein the propylene polymer is a propylene/α-olefin random copolymer.

TABLE 2

| | | | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 |
|---|---|---|---|---|---|---|---|---|---|---|
| Nozzles | Nozzle type | | Solid | Hollow | Hollow | Hollow | Solid | Solid | Hollow | Solid |
| | Canal width/pore area | mm$^{-1}$ | — | 0.41 | 0.41 | 0.41 | — | — | 0.28 | — |
| Materials | Kind | | PP-1 | PP-1 | PP-1 | PP-1 | PP-1 | PP-3 | PP-1 | PP-1 |
| Fibers | Fiber diameter | μm | 14 | 15 | 21 | 15 | 15 | 18 | 15 | 15 |
| | Fineness | d | 1.3 | 1.3 | 2.4 | 1.2 | 1.4 | 2.1 | 1.4 | 1.2 |
| | Hollowness | % | — | 9 | 17.1 | 15 | — | — | 2 | 14 |
| | Orientation | — | 0.77 | 0.8 | 0.92 | 0.73 | 0.68 | 0.73 | 0.76 | 0.75 |
| | Single filament strength | gf/d | 2 | 1.8 | 2.1 | 2.2 | 2.4 | 2 | 2.3 | 2.2 |
| | Number of crimps | Crimps/25 mm | 0 | 0 | 0 | 0 | 0 | 0 | 0 | 0 |
| Nonwoven fabrics | Basis weight Total | g/m$^2$ | 15 | 15 | 15 | 15 | 15 | 15 | 15 | 13 |
| | SB | g/m | 15 | 15 | 15 | 15 | 15 | 15 | 15 | 12.3 |
| | MB | g/m$^2$ | 0 | 0 | 0 | 0 | 0 | 0 | 0 | 0.7 |
| | Degree of uniformity | — | — | 0.90 | 1.10 | 1.19 | 0.90 | 0.90 | 1.10 | 1.04 | 1.10 |
| | Strength MD | N/25 mm | 20 | 20.7 | 16.6 | 21.8 | 17.3 | 12.3 | 15.9 | 16.9 |
| | CD | N/25 mm | 5.6 | 6.3 | 7.4 | 6.2 | 6.6 | 3.6 | 4.8 | 5.1 |
| | Flexural rigidity MD | mm | 50 | 48 | 56 | 61 | 62 | 38 | 63 | 56 |
| | CD | mm | 24 | 30 | 38 | 30 | 25 | 22 | 28 | 25 |
| | Water pressure resistance | mm Aqua | — | — | — | — | — | — | — | 172 |
| | KES FUKURAMI value | | 2.12 | 1.98 | 1.55 | 2.22 | 2.01 | −1.03 | 1.88 | — |

INDUSTRIAL APPLICABILITY

The spunbonded nonwoven fabrics according to the present invention exhibit excellent uniformity, high strength and flexibility even in the case where the fiber diameter of hollow fibers is reduced to 20 μm or less as well as where the basis weight is reduced. Sufficient strength can be ensured even if the basis weight is decreased to a lower level than conventional. Thus, the nonwoven fabrics can be made advantageously lightweight and can be suitably used in materials such as medical materials, industrial materials, civil engineering and building materials, agricultural and gardening materials, and daily life materials, in detail, can be widely used in products such as surgical gowns, bandages, 4. A nonwoven fabric laminate comprising the spunbonded nonwoven fabric described in claim 1.

5. A sanitary product comprising the nonwoven fabric laminate described in claim 4.

6. A nonwoven fabric laminate comprising the spunbonded nonwoven fabric described in claim 1, and a meltblown nonwoven fabric laminated thereto.

7. The nonwoven fabric laminate according to claim 6, wherein the meltblown nonwoven fabric comprises polyolefin fibers and has (i) an average fiber diameter of not more than 2.0 μm, (ii) a coefficient of variation of fiber diameter (CV) of not more than 60%, and (iii) a number of fusion bonding per 100 fibers of not more than 15.

8. A sanitary product comprising the nonwoven fabric laminate described in claim 7.

9. The nonwoven fabric laminate according to claim 6, wherein the meltblown nonwoven fabric comprises propylene polymer fibers and has (i) an average fiber diameter of not more than 2.0 µm, (ii) a coefficient of variation of fiber diameter (CV) of not more than 60%, and (iv) an $\alpha$-crystal fraction of less than 0.9.

10. A sanitary product comprising the nonwoven fabric laminate described in claim 9.

11. A sanitary product comprising the nonwoven fabric laminate described in claim 6.

12. A disposable diaper utilizing the spunbonded nonwoven fabric described in claim 1.

13. The spunbonded nonwoven fabric according to claim 1, wherein the hollow fibers have an eccentric hollow.

* * * * *